US008722089B2

(12) United States Patent
Chen

(10) Patent No.: US 8,722,089 B2
(45) Date of Patent: May 13, 2014

(54) DIP COATED COMPOSITIONS CONTAINING A STARCH HAVING A HIGH AMYLOSE CONTENT

(75) Inventor: Jen-Chi Chen, Morrisville, PA (US)

(73) Assignee: McNeil-PPC, Inc., Skillman, NJ (US)

(*) Notice: Subject to any disclaimer, the term of this patent is extended or adjusted under 35 U.S.C. 154(b) by 440 days.

(21) Appl. No.: 12/372,043

(22) Filed: Feb. 17, 2009

(65) Prior Publication Data

US 2009/0208574 A1    Aug. 20, 2009

Related U.S. Application Data

(60) Provisional application No. 61/029,691, filed on Feb. 19, 2008.

(51) Int. Cl.
*A61K 9/20* (2006.01)
*A61K 9/28* (2006.01)
*A61K 9/34* (2006.01)
*A61K 9/36* (2006.01)

(52) U.S. Cl.
CPC .................................. *A61K 9/2893* (2013.01)
USPC ............ 424/474; 424/464; 424/479; 424/481

(58) Field of Classification Search
None
See application file for complete search history.

(56) References Cited

U.S. PATENT DOCUMENTS

| | | | |
|---|---|---|---|
| 3,185,626 A | 5/1965 | Baker | |
| 4,543,370 A | 9/1985 | Porter et al. | |
| 4,643,894 A | 2/1987 | Porter et al. | |
| 4,683,256 A | 7/1987 | Porter et al. | |
| 4,725,441 A | 2/1988 | Porter et al. | |
| 4,802,924 A | 2/1989 | Woznicki et al. | |
| 4,820,524 A | 4/1989 | Berta | |
| 4,828,841 A | 5/1989 | Porter et al. | |
| 4,851,226 A | 7/1989 | Julian et al. | |
| 4,906,478 A | 3/1990 | Valentine et al. | |
| 5,075,114 A | 12/1991 | Roche et al. | |
| 5,198,227 A | 3/1993 | Batista | |
| 5,228,916 A | 7/1993 | Berta | |
| 5,234,099 A | 8/1993 | Bert | |
| 5,275,822 A | 1/1994 | Valentine et al. | |
| 5,296,233 A | 3/1994 | Batista et al. | |
| 5,436,026 A | 7/1995 | Berta et al. | |
| 5,489,436 A | 2/1996 | Hoy et al. | |
| 5,538,125 A | 7/1996 | Berta | |
| 5,630,871 A | 5/1997 | Jordan | |
| 5,658,589 A | 8/1997 | Parekh et al. | |
| 5,679,406 A | 10/1997 | Berta | |
| 5,770,225 A | 6/1998 | Parekh et al. | |
| 6,103,260 A | 8/2000 | Luber et al. | |
| 6,214,452 B1 | 4/2001 | Albrecht et al. | |
| 6,274,162 B1 | 8/2001 | Steffenino et al. | |
| 6,579,953 B1 | 6/2003 | Gotsche et al. | |
| 6,607,748 B1* | 8/2003 | Lenaerts et al. | ............. 424/464 |
| 7,785,650 B2 | 8/2010 | Gulian et al. | |
| 2003/0068372 A1 | 4/2003 | Kirschner et al. | |
| 2003/0070584 A1 | 4/2003 | Gulian et al. | |
| 2003/0072729 A1 | 4/2003 | Szymczak et al. | |
| 2003/0072731 A1 | 4/2003 | Gulian et al. | |
| 2003/0099692 A1* | 5/2003 | Lydzinski et al. | ............. 424/443 |
| 2004/0156902 A1 | 8/2004 | Lee et al. | |
| 2005/0107498 A1 | 5/2005 | Kolter et al. | |
| 2005/0152970 A1 | 7/2005 | Rinker et al. | |
| 2005/0233048 A1* | 10/2005 | Kitamura et al. | ............. 426/578 |
| 2007/0110799 A1* | 5/2007 | Leferve et al. | ................ 424/451 |
| 2009/0092739 A1 | 4/2009 | Gulian et al. | |

FOREIGN PATENT DOCUMENTS

| | | |
|---|---|---|
| CN | 1388190 A | 1/2003 |
| EP | 1 260 218 A | 11/2002 |
| EP | 1260218 A2 * | 11/2002 |
| EP | 1 570 843 A | 9/2005 |
| EP | 1260219 | 4/2009 |
| WO | WO 02/00205 A | 1/2002 |
| WO | WO 02/092708 A | 11/2002 |
| WO | WO 2008/012573 | 1/2008 |

OTHER PUBLICATIONS

Ratnayake Wajira S et al: "Pea Starch: Composition, structure and properties: A review", Jun. 1, 2002 (Jun. 1, 2002), Starke-Starch, Wiley-Vch Verlag, Weinheim, DE, pp. 217-234, XP002547247 ISSN: 0038-9056, p. 220; table 1.
PCT International Search Report for PCT/US2009/034243 dated Jan. 2, 2010.
Banker, G., et al. "Tablets", The Theory and Practice of Industrial Pharmacy, (Lachman et al.) Chapter 11, pp. 293 (1986).
Fegley, K., et al., "The Effect of Tablet Shape on the Perception of High Glass Film-Coating Systems", Colorcon (West Point, PA USA) (2002) Abstract.
Hilbert G., et al. "Pea Starch, A Starch of High Amylose Content", J.Biol Chemistry 162(2):229 (1946).
Official Monographs, USP #24 "Acetaminophen", (2000) p. 19-20 and 856 (1999).
Remington, "The Science and Practice of Pharmacy" edited by Alfonso Gennaro, $20^{th}$ ed., p. 1625 (2000).
Remingnton, "The Science and Practice of Pharmacy" Chapter 45, edited by Alfonso Gennaro, $20^{th}$ ed., p. 858 (2000).
Tricor Systems Inc., Model 805A806H Surface Analysis System Reference Manual (1996).
Williams, P., et al., "A Rapid Colorimetric Procedure for Estimating the Amylose Content of Starches and Flours", Cereal Chemistry 47:411-20 (1970).
Remington, "The Science and Practice of Pharmacy" edited by Alfonso Gennaro, $20^{th}$ ed. (2000), p. 1625-30.
Remington, "The Science and Practice of Pharmacy", Chapter 45, edited by Alfonso Gennaro, $20^{th}$ ed. (2000), p. 858-893.

* cited by examiner

*Primary Examiner* — Susan Tran
(74) *Attorney, Agent, or Firm* — William E. McGowan

(57) ABSTRACT

The present invention features a method of making a coated tablet by dipping a core comprising an active agent into a coating liquid and drying said dipped core to form a outer-coating on the core, wherein the coating liquid contains at least one a starch having an amylose content of at least about 50 percent by weight of said starch.

17 Claims, No Drawings

US 8,722,089 B2

DIP COATED COMPOSITIONS CONTAINING A STARCH HAVING A HIGH AMYLOSE CONTENT

CROSS-REFERENCE TO RELATED APPLICATION

The present application claims the benefit of priority to U.S. Provisional Application Ser. No. 61/029,691, filed Feb. 19, 2008, the contents of which are completely incorporated by reference

BACKGROUND OF THE INVENTION

Hard gelatin capsules were traditionally a popular dosage form for prescription and over-the-counter (OTC) drugs, and many patients preferred capsules over tablets, perceiving them as being easier to swallow. An alternative to capsule products are caplets, which are solid, oblong tablets that are often coated with various polymers such as cellulose ethers to improve their aesthetics, stability, and swallowability. Typically, such polymers are applied to the tablets either from a solution in organic solvents, or from an aqueous solution or dispersion via spraying. However, such spray-coated tablets lack the shiny surface and elegance of the hard gelatin capsules. Additionally, it is not commercially feasible to spray-coat a caplet with a different color coating on each end.

Another alternative to capsule products are gelcaps, which are elegant, shiny, consumer-preferred dosage forms that are prepared by dipping each half of an elongated tablet into two different colors of gelatin solution. See U.S. Pat. Nos. 4,820,524; 5,538,125; 5,770,225; 5,198,227; and 5,296,233, which are all incorporated by reference herein. A similar dosage form, commercially available as a "geltab," is prepared by dipping each half of a round, convex tablet into different colors of gelatin solution, as described in U.S. Pat. Nos. 5,228,916, 5,436,026 and 5,679,406, which are all incorporated by reference herein.

However, the use of gelatin as a pharmaceutical coating material presents certain disadvantages and limitations, including the potential for a decrease in the dissolution rate after extended storage, due to the cross-linking of the gelatin, and potential for microbial contamination of the gelatin solution during processing.

It is desirable to find a dip coating material, which not only produces a similar elegant, shiny, high gloss, consumer-preferred dosage form similar to that of gelatin-coated forms, but which is absent the limitations of gelatin, particularly those noted above.

SUMMARY OF THE INVENTION

In one aspect, the present invention features a method of making a coated tablet by dipping a core comprising an active agent into a coating liquid and drying said dipped core to form a outer-coating on the core, wherein the coating liquid contains at least one starch having an amylose content of at least about 50 percent by weight of said starch.

In one aspect, the present invention features a method of making a coated tablet by dipping a core comprising an active agent into a coating liquid and drying said dipped core to form a outer-coating on the core, wherein the coating liquid contains pea starch.

Other aspects, features, and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments can be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified.

DEFINITIONS

As used herein, "tablets," as used herein, refer to compressed or molded solid dosage forms of any shape or size. "Caplets," as used herein, refer to solid, oblong-shaped tablets.

"Water soluble," as used herein in connection with non-polymeric materials, shall mean from sparingly soluble to very soluble, i.e., not more than 100 parts water required to dissolve 1 part of the non-polymeric, water soluble solute. See Remington: The Science and Practice of Pharmacy, ed. Alfonso R. Gennaro, pp. 1625-30 ($20^{th}$ Ed, 2000). "Water soluble," as used herein in connection with polymeric materials, shall mean that the polymer swells in water and can be dispersed at the molecular level to form a homogeneous dispersion or colloidal "solution."

Coating Liquid

As discussed above, in one embodiment, the present application relates to a method of making a coated tablet by dipping a core comprising an active agent into a coating liquid. The coating liquid includes at least one starch having an amylose content of at least about 50 percent by weight of said starch. In one embodiment, the coating liquid may further include at least one gum and/or at least one plasticizer. The dipped core is then dried (e.g., to allow the liquid medium to be removed), following which the coating liquid formed an outer-coating on the core, resulting in a coated tablet.

In one embodiment, the coating liquid includes at least one gum, and the weight ratio of the at least one starch (i.e., the total combined weight of such starches if more than one type is included) to the at least one gum (i.e., the total combined weight of such gums if more than one type is included) is from about 250:1 to about 100:1 (such as from about 200:1 to about 150:1). In one embodiment, the coating liquid includes at least one plasticizer and the weight ratio of the at least one starch (i.e., the total combined weight of such starches if more than one type is included) to the at least one plasticizer (i.e., the total combined weight of such plasticizers if more than one type is included) is from about 20:1 to about 2:1 (such as from about 15:1 to about 3:1).

In one embodiment, the coating liquid is in the form of a dispersion. In one embodiment, the coating liquid includes a liquid medium in an amount, based upon the total weight of the coating liquid, from about 50 percent to about 85 percent (such as from about 55 percent to about 80 percent, such as from about 60 percent to about 75 percent). Examples of suitable liquid mediums include, but are not limited to: water; alcohols such as methanol, ethanol, and isopropanol; organic solvents such as methylene chloride, acetone, and the like; and mixtures thereof. In one embodiment, the liquid medium includes water. The resulting film forming dispersion typically possesses a solids level of, based upon the total weight of the film forming dispersion, from about 15 percent to about 50 percent, for example, from about 20 percent to about 45 percent or from about 25 percent to about 35 percent.

In one embodiment, the coating liquid comprises, based upon the total weight of the coating liquid, (i) from about 10 percent to about 40 percent (such as from about 20 to about 30 percent by weight) of the at least one starch; (ii) optionally from about from about 1 percent to about 15 percent (such as from about 1.5 percent to about 10 percent) of the at least one plasticizer; and (iii) optionally, from about 0.01 percent to about 0.5 percent (such as from about 0.05 to about 0.25 percent) of at least one gum.

In one embodiment, the viscosity of the coating liquid is from about 400 to about 3000 cps, such as from about 1000 cps to about 1800 cps, such as from about 1300 to about 1500 cps using a Brookfield viscometer, equipped with spindle #31, at 45° C.

In one embodiment, the resulting coating comprises, based upon the total dried weight of the outer-coating, (i) from about 70 percent to about 99 percent (such as from about 80 percent to about 95 percent) of the at least one starch; (ii) optionally, from about 0.5 percent to about 25 percent (such as from about 5 percent to about 10 percent) of a plasticizer; and (iii) optionally, from about 0.05 percent to about 1 percent (such as from about 0.1 percent to about 0.75 percent) of the at least one gum.

In one embodiment the coating liquid and subsequent dried coating are substantially free of gelatin. By substantially free, it is defined herein as less than 1 percent (such as contains less than about 0.1%, such as less than 0.01%, such as contains 0%). In another embodiment, the coating liquid and resulting outer-coating is substantially free of bovine derived materials. In another embodiment, the coating liquid and resulting outer-coating is substantially free of hydrocolloids. In another embodiment, the coating liquid and resulting outer-coating is substantially free of plasticizers. In another embodiment, the coating liquid and resulting outer-coating is substantially free of guar gum.

It has surprisingly been found that substrates may be dipped into such coating liquids of the present invention using the same equipment and similar range of process conditions as used for the production of dip molded, gelatin-coated tablets. For example, tablets may be coated using the aqueous dispersions of the present invention via known gelatin-dipping process parameters and equipment. Details of such equipment and processing conditions are known in the art and are disclosed at, for example, U.S. Pat. No. 4,820,524, which is incorporated by reference herein. The coating liquids disclosed herein can also advantageously be prepared at percent solids levels which are substantially higher than those that can be used for coating liquids containing other types of polymers such as hydrocolloids.

We have unexpectedly found that the coatings formed by dipping cores into the coating liquids of the present invention possessed excellent properties comparable to those possessed by gelatin coatings, e.g. crack resistance, hardness, thickness, color uniformity, smoothness, and gloss. Typically, the resulting outer-coatings of the present invention possessed a surface gloss of greater than about 150, e.g. greater than about 190, such as greater than about 210 or greater than 250.

In addition, tablets dip coated with the coating liquids of the present invention were superior to tablets dip coated with conventional gelatin-based coatings in several important ways. The dried coatings comprised of the compositions of the present invention also surprisingly and advantageously contained fewer air bubbles relative to the amount present in dried, gelatin based dipping compositions. Also, the dip coated compositions of the present invention possessed a higher degree of glossiness relative to similar coatings applied via spray coating methods known in the art. The dip coated compositions of the present invention also possessed a similar degree of glossiness relative to that possessed by gelatin-containing dip or enrobing coatings, which are currently viewed as the industry benchmark for high gloss coatings. See, e.g., U.S. Pat. No. 6,274,162 (Typical gloss readings for standard, commercially available gel-dipped or gelatin enrobed tablets range from about 200 to 240 gloss units, gloss readings for standard, commercially available sugar-coated medicaments range from 177 to 209 gloss units, and gloss readings for a new, high-gloss coating system range from about 148 to about 243 gloss units.).

Starch with High Amylose Content

Starches are biopolymer systems typically comprising predominantly two polysaccharides—amylose and amylopectin. As discussed above, the coating liquid and resulting outer-coating for the tablet includes a starch having an amylose content of at least about 50 percent (such as at least about 60 percent) by weight of the starch. What is meant by "amylose content" is the percent by weight of amylose contained in the starch The amylose content of starches may be measured using analysis known in the art (e.g., as set-forth in by Williams, P C et al, "A rapid calorimetric procedure for estimating the amylose contents on starch and flours. *Cereal Chemistry*, 47: 411-20 (1970)). The term "starch" includes both unmodified starches as well as starches in which functional groups of such starch have be modified, such as the addition of $C_2$-$C_8$ hydroxy alkyl groups (e.g., hydroxy propyl or hydroxy ethyl groups).

Examples of starches having an amylose content of at least about 50 percent by weight of the starch include starches derived from a pea (hereinafter referred to as "pea starches"). The term "pea starch" includes both unmodified pea starches as well as pea starches in which functional groups (e.g., the hydroxyl groups) of such starch have be modified (e.g., the substitution of $C_2$-$C_8$ hydroxy alkyl groups, such as hydroxy propyl or hydroxy ethyl groups). Examples of such modified pea starches includes Lycoat RS780®, wherein 6.2 percent of the hydroxyl groups of the pea starch have been substituted with a hydroxypropyl (available from Roquette Freres, 62136 Lestrem France).

Plasticizer

The coating liquid and resulting outer-coating for the dosage form includes one or more plasticizers. Examples of suitable plasticizers include, but are not limited to, glycerin, polyethylene glycol, propylene glycol, triethylcitrate, and tributyl citrate. Suitable plasticizers help prevent cracking of the resulting coating during the drying process.

Gum

As discussed above, the coating liquid and resulting outer-coating for the tablet includes one or more gums. Examples of such gums include, but are not limited to, xanthan gum, locust bean gum, and tara gum, and mixtures thereof. In one embodiment, the coating liquid and resulting outer-coating for the tablet includes a first gum and a second gum. In one embodiment, the first gum is xanthan gum and the second gun is locust bean gum.

Suitable xanthan gums include those available from C. P. Kelco Company (Atlanta, Ga.) under the tradename, "Keltrol 1000," "Xantrol 180," or "K9B310." Suitable locust bean gums include those available from LBG Sicilia (Ragusa, Italy).

Non-Gum Thickener

In one embodiment, the coating liquid and resulting outer-coating for the tablet further includes one or more thickeners, wherein such thickener(s) are not a gum. Examples of such thickeners include, but are not limited to, carrageenan (such as lambda carageenan and kappa carageenan), polyethylene oxide, hypromellose, and hydroxypropylcellulose and mixtures thereof. In one embodiment, the resulting coating comprises, based upon the total dried weight of the outer-coating, from about 0.5 percent to about 2 percent of the one or more thickeners (e.g., carrageenan).

Other Ingredients

Optionally, the coating liquid and resulting outer-coating may include other ingredients such as, based upon the total weight of the coating liquid, from about 0 percent to about 2 percent preservatives such as methylparaben and propylparaben, from about 0 percent to about 14 percent opacifying agents such as titanium dioxide, and/or from about 0 percent to about 14 percent colorants. See *Remington: The Science and Practice of Pharmacy*, ed. Alfonso R. Gennaro, pp. 858-893 ($20^{th}$ Ed, 2000), which is herein incorporated by reference.

Examples of colorants include, but not be limited to azo dyes, quinopthalone dyes, triphenylmethane dyes, xanthene dyes, indigoid dyes, iron oxides, iron hydroxides, titanium dioxide, natural dyes, and mixtures thereof. More specifically, suitable colorants include, but are not limited to patent blue V, acid brilliant green BS, red 2G, azorubine, ponceau 4R, amaranth, D+C red 33, D+C red 22, D+C red 26, D+C red 28, D+C yellow 10, FD+C yellow 5, FD+C yellow 6, FD+C red 3, FD+C red 40, FD+C blue 1, FD+C blue 2, FD+C green 3, brilliant black BN, carbon black, iron oxide black, iron oxide red, iron oxide yellow, titanium dioxide, riboflavin, carotenes, antyhocyanines, turmeric, cochineal extract, clorophyllin, canthaxanthin, caramel, and betanin, and mixtures thereof.

In one embodiment the coating liquid and resulting outer-coating may include a sweetener. Suitable sweeteners include but are not limited to aspartame, acesulfame potassium, sucralose, and saccharin and mixtures thereof. A sweetener may be added to the coating by weight of the dried coating at a level of about 0.01 to about 30 percent, e.g. about 0.05 to about 5 percent, e.g. about 0.05 to about 3 percent.

In one embodiment the coating liquid and resulting outer-coating include an acidulant. Suitable acidulants include but are not limited to citric acid, malic acid, fumaric acid, and ascorbic acid and mixtures thereof. An acidulant may be added to the coating by weight of the dried coating at a level of about 0.01 to about 20 percent, e.g. about 0.05 to about 10 percent, e.g. about 0.05 to about 5 percent.

In one embodiment, the coating liquid and resulting outer-coating include a warming agent, flavoring agent or cooling agent. Examples of warming agents include but are not limited to capsaicin. Examples of cooling agents include but are not limited to volatile coolers such as menthol or monomenthyl succinate, or non volatile coolers such as that available from International Flavors and Fragrances (IFF) as "Cooler #2". A warming agent, flavoring agent and/or cooling agent may be added to the coating by weight of the dried coating at a level of about 0.005 to about 20 percent, e.g. about 0.01 to about 10 percent, such as about 0.01 to about 5 percent.

In one embodiment the coating liquid and resulting outer-coating include special effect pigments which are dispersed and not dissolved the liquid. Examples of special effect pigments include but are not limited to mica, candurin, silica flakes, aluminum flakes, gold flakes and titanium dioxide flakes and mixtures thereof. A special effect pigment may be added to the coating by weight of the dried coating at a level of about 0.01 to about 40 percent, e.g. about 0.05 to about 30 percent, e.g. about 0.05 to about 10 percent.

In one embodiment, the coating liquid and resulting outer coating contains salts that act in a buffering capacity to maintain pH levels. Suitable alts include, but are not limited to, phosphate salts, citrate salts (such as sodium and calcium citrate), and bicarbonate salts (such as sodium or potassium bicarbonate).

Core of the Coated Tablet

As discussed above, the coated tablet includes a core including a pharmaceutically active agent. The core may also optionally comprise a sub-core (which may also be referred to as an "insert"), which may be made by any method, for example compression or molding, and which may optionally contain one or more pharmaceutically active agents.

The core of the present invention may be prepared by any suitable method, including for example compression and molding, and depending on the method by which it is made, typically comprises pharmaceutically active agent(s) and a variety of excipients (such as inactive ingredients which may be useful for conferring desired physical properties to the dosage core).

In embodiments wherein the core is a compressed dosage form, for example, a compressed tablet, the core may be obtained from a compressed powder. The powder may contain an pharmaceutically active agent, and optionally comprise various excipients, such as binders, disintegrants, lubricants, fillers and the like, as is conventional, or the powder may comprise other particulate material of a medicinal or non-medicinal nature, such as inactive placebo blends for tableting, confectionery blends, and the like. One particular formulation comprises pharmaceutically active agent, as an excipient, a plastically deforming compressible material, and optionally other excipients, such as disintegrants and lubricants and is described in more detail in United States Patent Application Publication No. 20030068373. During compression, the plastically deforming compressible material assumes the shape of the microrelief from the upper and/or lower punch surface.

Suitable plastically deforming compressible materials for these embodiments include, but are not limited to: microcrystalline cellulose, waxes, fats, mono- and di-glycerides, derivatives and mixtures thereof, and the like. In certain embodiments, wherein the plastically deforming compressible material is later caused to melt and be absorbed into the tablet, the plastically deforming compressible material may be selected from low-melting plastically deforming compressible materials, such as plastically deforming compressible powdered waxes, such as shellac wax and microcrystalline wax, polyethylene glycol, and mixtures thereof.

Suitable fillers include, but are not limited to, water-soluble compressible carbohydrates such as sugars, which include dextrose, sucrose, isomaltalose, fructose, maltose, and lactose, polydextrose, sugar-alcohols, which include mannitol, sorbitol, isomalt, maltitol, xylitol, erythritol, starch hydrolysates, which include dextrins, and maltodextrins, and the like, water insoluble plastically deforming materials such as microcrystalline cellulose or other cellulosic derivatives, water-insoluble brittle fracture materials such as dicalcium phosphate, tricalcium phosphate and the like and mixtures thereof.

Suitable binders include, but are not limited to, dry binders such as polyvinyl pyrrolidone, hydroxypropylmethylcellulose, and the like; wet binders such as water-soluble polymers, including hydrocolloids such as alginates, agar, guar gum, locust bean, carrageenan, tara, gum arabic, tragacanth, pectin, xanthan, gellan, maltodextrin, galactomannan, pusstulan, pullulan, laminarin, scleroglucan, gum arabic, inulin, pectin, whelan, rhamsan, zooglan, methylan, chitin, cyclodextrin, chitosan, polyvinyl pyrrolidone, cellulosics, starches, and the like; and mixtures thereof.

Suitable disintegrants include, but are not limited to, sodium starch glycolate, cross-linked polyvinylpyrrolidone, cross-linked carboxymethylcellulose, starches, microcrystalline cellulose, and the like.

Suitable lubricants include, but are not limited to, long chain fatty acids and their salts, such as magnesium stearate and stearic acid, talc, and waxes.

Suitable glidants include, but are not limited to, colloidal silicon dioxide, and the like.

In embodiments in which the core is prepared via compression, the core may also incorporate pharmaceutically acceptable adjuvants, including, but not limited to preservatives, high intensity sweeteners such as aspartame, acesulfame potassium, cyclamate, saccharin, sucralose, and the like; and other sweeteners such as dihydroalcones, glycyrrhizin, Monellin™, stevioside, Talin™, and the like; flavors, antioxidants, surfactants, and coloring agents.

In one embodiment of the invention, the dosage forms of this invention comprise a core made from a blend of powders having an average particle size of about 50 microns to about 500 microns. In one embodiment, the pharmaceutically active agent has an average particle size of about 50 microns to about 500 microns. In another embodiment, at least one excipient has an average particle size of about 50 microns to about 500 microns, e.g. about 100 to about 500 microns. In one such embodiment, a major excipient (e.g., an excipient comprising at least 50% by weight of the core), has an average particle size of about 50 microns to about 500 microns (such as about 100 to about 500 microns). Particles in this size range are particularly useful for direct compression processes.

In one embodiment of the invention, the core may be a directly compressed tablet made from a powder that is substantially free of water-soluble polymeric binders and hydrated polymers. This composition is advantageous for maintaining an immediate release dissolution profile, minimizing processing and material costs, and providing for optimal physical and chemical stability of the dosage form. In one embodiment the density of the dosage form is greater than about 0.9 g/cc. In one embodiment the hardness of the dosage form is greater than about 7 kiloponds, e.g. greater than about 9 kiloponds when tested using the Schleuniger Hardness Tablet Tester. The Schleuniger Hardness Tablet Tester functions by compressing 2 opposing metal clamps, which in turn applies a force to a single tablet until a breakage is detected, at which point the force of breakage is measured in kiloponds or kilopascals. The average of 5 tablets is recorded.

In embodiments in which the core is prepared by direct compression, the materials comprising the core, e.g. the pharmaceutically active agent(s) and excipient(s), may be blended together, for example as dry powders, and fed into a cavity of an apparatus that applies pressure to form a core. Any suitable compacting apparatus may be used, including for example a roller compactor such as a chilsonator or drop roller; or a conventional tablet press. In one embodiment, the core may be formed by compaction using a rotary tablet press as known in the art. In general, a metered volume of powder is filled into a die cavity of the rotary tablet press, and the cavity rotates as part of a "die table" from the filling position to a compaction position. At the compaction position, the powder is compacted between an upper and a lower punch, then the resulting tablet is pushed from the die cavity by the lower punch. Advantageously, the direct compression process enables the minimization or elimination of water-soluble, non-saccharide polymeric binders such as polyvinyl pyrrolidone, alginates, hydroxypropyl cellulose, hydroxypropylmethylcellulose, hydroxyethylcellulose, and the like, which could have a negative effect on dissolution.

In another embodiment, the core may be prepared by the compression methods and apparatus described in United States Patent Application Publication No. 20040156902. Specifically, the core may be made using a rotary compression module comprising a fill zone, insertion zone, compression zone, ejection zone, and purge zone in a single apparatus having a double row die construction. The dies of the compression module may then be filled using the assistance of a vacuum, with filters located in or near each die. The purge zone of the compression module includes an optional powder recovery system to recover excess powder from the filters and return the powder to the dies.

In another embodiment, the core may be prepared by a wet-granulation method, in which the pharmaceutically active agent, appropriate excipients, and a solution or dispersion of a wet binder (e.g., an aqueous cooked starch paste or solution of polyvinyl pyrrolidone) may be mixed and granulated. Suitable apparatus for wet granulation include low shear (e.g., planetary mixers), high shear mixers, and fluid beds (including rotary fluid beds). The resulting granulated material may then be dried, and optionally dry-blended with further ingredients (e.g., adjuvants and/or excipients such as, for example, lubricants, colorants, and the like). The final dry blend is then suitable for compression by the methods described in the previous paragraph. Methods for direct compression and wet granulation processes are known in the art.

Subcoating of the Core

In one embodiment, core comprises one or more subcoating layers. In one embodiment, the subcoating layer substantially covers the surface of the core. The use of subcoatings is well known in the art and disclosed in, for example, U.S. Pat. No. 3,185,626, which is incorporated by reference herein. Examples of suitable subcoatings are disclosed in U.S. Pat. Nos. 4,683,256, 4,543,370, 4,643,894, 4,828,841, 4,725,441, 4,802,924, 5,630,871, and 6,274,162, which are all incorporated by reference herein. Suitable subcoatings may include one or more of the following ingredients: cellulose ethers such as hydroxypropylmethylcellulose, hydroxypropylcellulose, and hydroxyethylcellulose; polycarbohydrates such as xanthan gum, starch, and maltodextrin; plasticizers including for example, glycerin, polyethylene glycol, propylene glycol, dibutyl sebecate, triethyl citrate, vegetable oils such as castor oil, surfactants such as polysorbate-80, sodium lauryl sulfate and dioctyl-sodium sulfosuccinate; polycarbohydrates, pigments, and opacifiers.

In one embodiment, the subcoating includes, based upon the total weight of the subcoating, from about 2 percent to about 8 percent, e.g. from about 4 percent to about 6 percent of a water-soluble cellulose ether and from about 0.1 percent to about 1 percent, castor oil, as disclosed in detail in U.S. Pat. No. 5,658,589, which is incorporated by reference herein. In another embodiment, the subcoating includes, based upon the total weight of the subcoating, from about 20 percent to about 50 percent (such as from about 25 percent to about 40 percent) of HPMC; from about 45 percent to about 75 percent (such as from about 50 percent to about 70 percent) of maltodextrin; and from about 1 percent to about 10 percent (such as from about 5 percent to about 10 percent) of PEG 400.

The subcoating typically is present in an amount, based upon the dry weight of the core, from about 0 percent to about 5 percent. The dried dip coating layer typically is present in an amount, based upon the dry weight of the core and the optional subcoating, from about 1.5 percent to about 10 percent.

In one embodiment the coated tablet is substantially free of a subcoating.

In one embodiment wherein the coated tablet includes one or more openings through the coating of the coated tablet that extend to the core of the coated tablet, the coated tablet is substantially free of a subcoating.

In one embodiment wherein the coated tablet includes both a subcoating and an outer coating, the outer coating does not coat the belly-band of the caplet (e.g., exposing a portion of the subcoating). In one embodiment, the belly-band exposes a portion of the subcoating having a width of at least 2 mm. In one embodiment, the gloss level of the outer-coating is at least 10 percent (such as at least 20 percent) greater than the gloss level of the exposed subcoating.

Outer-Coating of the Coated Tablet

What is meant by outer-coating is the coating on the outer surface of the coated tablet. In one embodiment, the outer-coating substantially covers (i.e., covers at least 90 percent) the surface of said core.

The average thickness of the dried dip-coating layer typically is from about 40 to about 400 microns. However, one skilled in the art would readily appreciate without undue experimentation that the dip coating thickness may be varied in order to provide a smoother, easier to swallow, dosage form or to achieve a desired dissolution profile. Moreover, the thickness of dipped film coatings may vary at different locations on the substrate depending upon its shape. For example, the thickness of the coating at an edge or corner of a substrate may be as much as 50 percent to 70 percent less than the thickness of the coating at the center of a major face of the substrate. This difference can be minimized by, for example, use of a thicker subcoating, or use of dipping compositions that result in higher weight gains on the substrate.

In embodiments wherein a thicker dip coating is desired, we have found that an effective amount of a weight gain enhancer selected from the group consisting of simethicone, polysorbate 80 and mixtures thereof, may be added to a film forming composition comprised, consisting of, and/or consisting essentially of a film former and an optional thickener such as a hydrocolloid. The weight gain enhancer is used in an amount sufficient to increase the weight gain of the coating liquid, e.g. by at least about 10 percent, by at least about 20%, or by at least about 30% on a substrate when dried. The percent weight gain increase is determined based upon the difference between the total weight of the coated substrate with the coating composition including the weight gain enhancer, and the total weight of an coated equivalent substrate, which has been coated under similar processing conditions with a coating composition that does not include an effective amount of weight gain enhancer.

In one embodiment, the method further comprises creating one or more openings in the subcoating in the portion of the tablet that is not coated with the outer-coating, to expose said core on the surface of said coated tablet, such as described in US Patent Application No. 2005/0152970.

In one embodiment, the method further comprises creating one or more openings in the outer-coating to expose the core, not through the subcoating, as disclosed in US Patent Application No. 2005/0152970, but through the portion of the tablet containing the outer-coating. This is advantageous since the outer-coating disclosed herein is compatible with laser drilling, whereas gelatin is not compatible. Since gelatin is not compatible with laser drilling, it is necessary in tablets with such gelatin coating, to expose the subcoat before laser drilling the openings.

In one embodiment the outer-coating covers only a portion of the tablet such as only one half of the coated tablet. The other half of the tablet may comprise a separate type of the outer-coating such as gelatin, or expose only the subcoat or core.

In one embodiment, the outer coating is substantially free of colorants. As used in this embodiment, substantially free is defined as less than 1% by weight, such as less than 0.5% by weight of colorant(s). In one embodiment, the core is a bilayer core (wherein one layer includes a first color and the second layer includes a second color) and the coating is translucent. In one embodiment, the second layer comprises an active ingredient which is the same or different from the active ingredient in the first layer. One layer may have an immediate release pharmaceutically active agent, and the other layer may have a modified release pharmaceutically active agent.

In one embodiment, the outer coating is translucent and comprises a colorant. In one embodiment, the outer coating is translucent and is substantially free of a colorant.

Surface Gloss of Outer-Coating of Coated Tablet

In one embodiment, the outer-coating possesses a surface gloss of at least 150. "Surface gloss" as used herein, shall refer to amount of light reflectance as measured at a 60 degree incident angle using the method set forth in Example 8 herein.

Capsule-Like Coated Tablets

In one embodiment, the coated tablets resemble a multi-colored capsule (e.g., a coated tablet having one end with an outer-coating of one color and the other end with an outer-coating of a different color). See U.S. Pat. No. 4,820,524, which is incorporated by reference herein.

In one embodiment, the method includes dipping the first end of the core into a first coating liquid and then further includes dipping said second end of the core into a second coating liquid, wherein the second coating liquid is a different color from said coating liquid.

In one embodiment, the coated tablet includes a subcoating and an outer coating, wherein the outer coating surrounds from about 40 percent to about 60 percent of surface area of the core.

In one embodiment, the dosage form is a simulated capsule like medicament comprising a subcoating and an outer coating on two ends of the tablet, wherein the outer coating portions come together or overlap. In one embodiment, the dosage form is a simulated capsule like medicament comprising a subcoating and an outer coating on two ends of the tablet, wherein the outer coating portions do not overlap, thereby exposing a portion of the subcoating. In one embodiment, at least one opening is provided through the exposed subcoated portion to the core and/or and at least one opening is provided through the outer coating to the core.

Pharmaceutically Active Agent

The dosage form of the present invention includes at least one pharmaceutically active agent. What is meant by a "pharmaceutically active agent" is an agent (e.g., a compound) that is permitted or approved by the U.S. Food and Drug Administration, European Medicines Agency, or any successor entity thereof, for the oral treatment of a condition or disease. Suitable pharmaceutically active agents include, but are not limited to, analgesics, anti-inflammatory agents, antihistamines, antibiotics (e.g., antibacterial, antiviral, and antifungal agents), antidepressants, antidiabetic agents, antispasmodics, appetite suppressants, bronchodilators, cardiovascular treating agents (e.g., statins), central nervous system treating agents, cough suppressants, decongestants, diuretics, expectorants, gastrointestinal treating agents, anesthetics, mucolytics, muscle relaxants, osteoporosis treating agents, stimulants, nicotine, and sedatives.

Examples of suitable gastrointestinal treating agents include, but are not limited to: antacids such as aluminum-containing active ingredients (e.g., aluminum carbonate, aluminum hydroxide, dihydroxyaluminum sodium carbonate, and aluminum phosphate), bicarbonate-containing active ingredients, bismuth-containing active ingredients (e.g., bismuth aluminate, bismuth carbonate, bismuth subcarbonate, bismuth subgallate, and bismuth subnitrate), calcium-containing active ingredients (e.g., calcium carbonate), glycine, magnesium-containing active ingredients (e.g., magaldrate, magnesium aluminosilicates, magnesium carbonate, magnesium glycinate, magnesium hydroxide, magnesium oxide, and magnesium trisilicate), phosphate-containing active ingredients (e.g., aluminum phosphate and calcium phosphate), potassium-containing active ingredients (e.g., potassium bicarbonate), sodium-containing active ingredients (e.g., sodium bicarbonate), and silicates; laxatives such as stool softeners (e.g., docusate) and stimulant laxatives (e.g., bisacodyl); H2 receptor antagonists, such as famotidine, ranitidine, cimetadine, and nizatidine; proton pump inhibitors such as omeprazole and lansoprazole; gastrointestinal cytoprotectives, such as sucraflate and misoprostol; gastrointestinal prokinetics such as prucalopride; antibiotics for *H. pylori*, such as clarithromycin, amoxicillin, tetracycline, and metronidazole; antidiarrheals, such as bismuth subsalicylate, kaolin, diphenoxylate, and loperamide; glycopyrrolate; analgesics, such as mesalamine; antiemetics such as ondansetron, cyclizine, diphenyhydroamine, dimenhydrinate, meclizine, promethazine, and hydroxyzine; probiotic bacteria including but not limited to *lactobacilli*; lactase; racecadotril; and antiflatulents such as polydimethylsiloxanes (e.g., dimethicone and simethicone, including those disclosed in U.S. Pat. Nos. 4,906,478, 5,275,822, and 6,103,260); isomers thereof; and pharmaceutically acceptable salts and prodrugs (e.g., esters) thereof.

Examples of suitable analgesics, anti-inflammatories, and antipyretics include, but are not limited to, non-steroidal anti-inflammatory drugs (NSAIDs) such as propionic acid derivatives (e.g., ibuprofen, naproxen, ketoprofen, flurbiprofen, fenbufen, fenoprofen, indoprofen, ketoprofen, fluprofen, pirprofen, carprofen, oxaprozin, pranoprofen, and suprofen) and COX inhibitors such as celecoxib; acetaminophen; acetyl salicylic acid; acetic acid derivatives such as indomethacin, diclofenac, sulindac, and tolmetin; fenamic acid derivatives such as mefanamic acid, meclofenamic acid, and flufenamic acid; biphenylcarbodylic acid derivatives such as diflunisal and flufenisal; and oxicams such as piroxicam, sudoxicam, isoxicam, and meloxicam; isomers thereof; and pharmaceutically acceptable salts and prodrugs thereof.

Examples of antihistamines and decongestants, include, but are not limited to, bromopheniramine, chlorcyclizine, dexbrompheniramine, phenindamine, pheniramine, pyrilamine, thonzylamine, pripolidine, ephedrine, phenylephrine, pseudoephedrine, phenylpropanolamine, chlorpheniramine, dextromethorphan, diphenhydramine, doxylamine, astemizole, terfenadine, fexofenadine, naphazoline, oxymetazoline, montelukast, propylhexadrine, triprolidine, clemastine, acrivastine, promethazine, oxomemazine, mequitazine, buclizine, bromhexine, ketotifen, terfenadine, ebastine, oxatamide, xylomeazoline, loratadine, desloratadine, and cetirizine; isomers thereof; and pharmaceutically acceptable salts and esters thereof.

Examples of cough suppressants and expectorants include, but are not limited to, diphenhydramine, dextromethorphan, noscapine, clophedianol, menthol, benzonatate, ethylmorphone, codeine, acetylcysteine, carbocisteine, ambroxol, belladona alkaloids, sobrenol, guaiacol, and guaifenesin; isomers thereof; and pharmaceutically acceptable salts and prodrugs thereof.

Examples of muscle relaxants include, but are not limited to, cyclobenzaprine and chlorzoxazone metaxalone, and orphenadrine, methocarbamol; isomers thereof; and pharmaceutically acceptable salts and prodrugs thereof.

Examples of stimulants include, but are not limited to, caffeine.

Examples of sedatives include, but are not limited to sleep aids such as antihistamines (e.g., diphenhydramine), eszopiclone, and zolpidem, and pharmaceutically acceptable salts and prodrugs thereof.

Examples of appetite suppressants include, but are not limited to, phenylpropanolamine, phentermine, and diethylcathinone, and pharmaceutically acceptable salts and prodrugs thereof Examples of anesthetics (e.g., for the treatment of sore throat) include, but are not limited to dyclonene, benzocaine, and pectin and pharmaceutically acceptable salts and prodrugs thereof.

Examples of suitable statins include but are not limited to atorvastin, rosuvastatin, fluvastatin, lovastatin, simvustatin, atorvastatin, pravastatin and pharmaceutically acceptable salts and prodrugs thereof.

As discussed above, the pharmaceutically active agents of the present invention may also be present in the form of pharmaceutically acceptable salts, such as acidic/anionic or basic/cationic salts. Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate and triethiodide. Pharmaceutically acceptable basic/cationic salts include, and are not limited to aluminum, benzathine, calcium, chloroprocaine, choline, diethanolamine, ethylenediamine, lithium, magnesium, meglumine, potassium, procaine, sodium and zinc.

As discussed above, the pharmaceutically active agents of the present invention may also be present in the form of prodrugs of the pharmaceutically active agents. In general, such prodrugs will be functional derivatives of the pharmaceutically active agent, which are readily convertible in vivo into the required pharmaceutically active agent. Conventional procedures for the selection and preparation of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

Where the pharmaceutically active agents according to this invention have at least one chiral center, they may accordingly exist as enantiomers. Where the pharmaceutically active agents possess two or more chiral centers, they may additionally exist as diastereomers. It is to be understood that all such isomers and mixtures thereof are encompassed within the scope of the present invention. Furthermore, some of the crystalline forms for the pharmaceutically active agents may exist as polymorphs and as such are intended to be included in the present invention. In addition, some of the pharmaceutically active agents may form solvates with water (i.e., hydrates) or common organic solvents, and such solvates are also intended to be encompassed within the scope of this invention.

In one embodiment, the pharmaceutically active agent or agents are present in the dosage form in a therapeutically effective amount, which is an amount that produces the desired therapeutic response upon oral administration and can be readily determined by one skilled in the art. In determining such amounts, the particular pharmaceutically active agent being administered, the bioavailability characteristics of the pharmaceutically active agent, the dose regime, the age and weight of the patient, and other factors must be considered, as known in the art.

The pharmaceutically active agent may be present in various forms. For example, the pharmaceutically active agent may be dispersed at the molecular level, e.g. melted, within the dosage form, or may be in the form of particles, which in turn may be coated or uncoated. If the pharmaceutically active agent is in form of particles, the particles (whether coated or uncoated) typically have an average particle size of from about 1 to about 2000 microns. In one embodiment, such particles are crystals having an average particle size of from about 1 to about 300 microns. In another embodiment, the particles are granules or pellets having an average particle size of from about 50 to about 2000 microns, such as from about 50 to about 1000 microns, such as from about 100 to about 800 microns.

If the pharmaceutically active agent has an objectionable taste, the pharmaceutically active agent may be coated with a taste masking coating, as known in the art. Examples of suitable taste masking coatings are described in U.S. Pat. No. 4,851,226, U.S. Pat. No. 5,075,114, and U.S. Pat. No. 5,489,436. Commercially available taste masked pharmaceutically active agents may also be employed. For example, acetaminophen particles which are encapsulated with ethylcellulose or other polymers by a coaccervation process may be used in the present invention. Coaccervation-encapsulated acetaminophen may be purchased commercially from Eurand America, Inc. (Vandalia, Ohio) or from Circa Inc. (Dayton, Ohio).

The pharmaceutically active agent may be present in pure crystal form or in a granulated form prior to the addition of the taste masking coating. Granulation techniques may be used to improve the flow characteristics or particle size of the pharmaceutically active agent to make it more suitable for compression or subsequent coating. Suitable binders for making the granulation include but are not limited to starch, polyvinylpyrrolidone, polymethacrylates, hydroxypropylmethylcellulose, and hydroxypropylcelllulose. The particles including pharmaceutically active agent(s) may be made by cogranulating the pharmaceutically active agent(s) with suitable substrate particles via any of the granulation methods known in the art. Examples of such granulation method include, but are not limited to, high sheer wet granulation and fluid bed granulation such as rotary fluid bed granulation, the details of which are disclosed in, "The Theory and Practice of Industrial Pharmacy, $3^{rd}$ edition", Chapter 11, Lachman, Leon et. al, 1986.

In one embodiment the pharmaceutically active agent is coated as particles for taste-masking purposes with a combination of a water insoluble film forming polymer (such as but not limited to cellulose acetate or ethylcellulose) and a water soluble polymer (such as but not limited to povidone, polymethacrylic copolymers such as those sold under the tradename Eudragit E-100 from Rohm America, and hydroxypropylcellulose). In this embodiment, the ratio of water insoluble film forming polymer to water soluble polymer is from about 50 to about 95 percent of water insoluble polymer and from about 5 to about 50 percent of water soluble polymer, and the weight percent of the coating by weight of the coated taste-masked particle is from about 5 percent to about 40 percent.

In one embodiment one or more pharmaceutically active agents or a portion of the pharmaceutically active agent may be bound to an ion exchange resin in the disintegrative tablet portion or the lozenge portion for the purposes of taste-masking the pharmaceutically active agent or delivering the active in a modified release manner.

In one embodiment, the pharmaceutically active agent is capable of dissolution upon contact with a fluid such as water, stomach acid, intestinal fluid or the like. In one embodiment, the dissolution characteristics of the pharmaceutically active agent within the disintegrative tablet portion meets USP specifications for immediate release tablets including the pharmaceutically active agent. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing, and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes after dosing. See USP 24, 2000 Version, 19-20 and 856 (1999). In another embodiment, the dissolution characteristics of the pharmaceutically active agent are modified: e.g. controlled, sustained, extended, retarded, prolonged, delayed and the like.

In one embodiment, the dosage forms coated with the dip coatings of the present invention provided for immediate release of the pharmaceutically active agent, i.e. the dissolution of the dosage form conformed to USP specifications for immediate release tablets containing the particular pharmaceutically active agent employed. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing, and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes after dosing. See USP 24, 2000 Version, 19-20 and 856 (1999).

EXAMPLES

Specific embodiments of the present invention are illustrated by way of the following examples. This invention is not confined to the specific limitations set forth in these examples.

Example 1

Preparation of Compressed Caplet Core Granulation 4.0 kg of the granulation materials in Table 1 are blended in a Glatt GCPG 5/9 top spray fluid bed coating unit (Glatt, Ramsey, N.J.). A granulating solution of 7% by weight of cornstarch NF in purified water is sprayed onto the blend inside of the coating unit (at a product temperature of 25-30° C. and an atomization air pressure of 2 bars) at approximately 20 g/minute and dried to a temperature of 35° C.

TABLE 1

Granulation Materials

| Granulation Material | Weight Percent of Granulation |
|---|---|
| Acetaminophen USP | 86.4 |
| Powdered Cellulose NF (Commercially available from Solka Floc as BW 40) | 5.6 |
| Microcrystalline Cellulose (Commercially Available from FMC as Avicel PH101) | 5.3 |
| Pregelatinized Starch NF | 1.9 |
| Sodium Starch Glycolate NF | 0.8 |

Example 2

Preparation of Blend for Compression 2475.5 g of the granulation prepared in Example 1 are placed into a twin-shell blender. 16.1 g of colloidal silicon dioxide NF, 54.3 g of stearic acid NF, 889 g of microcrystalline cellulose NF, and 65.1 g of sodium starch glycolate NF are added to the blend, blended end-over end for 10 minutes, and discharged into a plastic bag.

Example 3

Preparation of Compressed Core

The blend from Example 2 is compressed on a rotary lab tablet press (Manesty, Knowsley, Merseyside, UK) using caplet tooling of 0.75 inches×0.25 inches×0.075 inches at a hardness of 11.1 to 15.6 kiloponds, a weight of 575 to 609 mg, and a thickness of 6.01 mm to 6.21 mm.

Example 4

Preparation of Gray Film Coating Solution 340 g of sterile water for irrigation are added to a 2-liter stainless steel vessel. A laboratory mixer is set to 50 RPM, and 85 g of hypromellose based film coating polymer containing gray colorant are added and mixed for 45 minutes.

Example 5

Gray Film Coating of Cores 3 kg of caplets from each of Example 3 are added to a 24-inch vented Acela Cota® coating pan (Manesty). The batch is spray coated with a spray rate of approximately 12 grams per minute, about 14 RPM, an inlet air temperature of about 85° C., and an atomization air pressure of about 55 psi. 405 grams of the coating solution are sprayed on the caplets, which are equivalent to 81 g of dried coating or about a 2.7% weight gain.

Example 6

Preparation of Gelatin Replacement Formulation Coating (a) Preparation of Red Pea-Starch Based Dipping Solution
645 kg of sterile water for irrigation are added to a 50-gallon stainless steel vessel. With agitation at 80 RPM, 0.576 kg of locust bean gum and 0.806 kg of xanthan gum are added orderly. Then, the mixture is heated to 85° C. At 85° C., 248.417 kg of pea starch (Lycoat RS780®) are added and mixed for 1 hour. After that, 24.971 kg of glycerin, 1.658 kg of sodium lauryl sulfate, and 13.82 kg of red colorant are added. The solution is mixed at low speed for 4 hours (at ambient pressure) to deaerate while the tank is maintained at a solution temperature of about 45° C.

(b) Preparation of Blue Pea-Starch Based Dipping Solution
645 kg of sterile water for irrigation are added to a 50-gallon stainless steel vessel. With agitation at 80 RPM, 0.576 kg of locust bean gum and 0.806 kg of xanthan gum are added orderly. Then, the mixture is heated to 85° C. At 85° C., 248.417 kg of pea starch are added and mixed for 1 hour. After that, 24.971 kg of glycerin, 1.658 kg of sodium lauryl sulfate, and 13.82 kg of blue colorant are added. The solution is mixed at low speed for 4 hours (at ambient pressure) to deaerate while the tank is maintained at a solution temperature of about 45° C.

Example 7

Preparation of Coated Caplets with Pea Starch Based Coating (a) Lab Based Method
The subcoated caplets from Example 5 are coated with the solutions outlined in Example 6 with the following manual method. A polyethylene pipette is manually cut to fit the diameter of the caplet. The subcoated caplet is manually dipped into one of the solutions until approximately one half of the caplet is coated with the solution. The caplet is allowed to dry at 21-28° C. for approximately 30 minutes. The caplet is then removed from the holder and placed into another holder wherein the uncoated portion is exposed. This portion is then dipped into the other coating solution and removed and dried at 21-28° C. for approximately 30 minutes.

(b) Additional Color Combinations—Lab Based Method
Solutions are prepared using various color combinations of the pea starch-based solution made in accordance with the method in Example 6; including red/yellow colored caplets and clear coated caplets. Additional cores prepared in accordance with Example 5 are dipped manually using the same method described in Example 7(a).

(c) Manufacturing Method-Dipping of Subcoated Cores to Prepare the Dosage Form of the Invention
Part (1):
96 kg of a blue pea starch based dipping solution prepared in accordance with Example 6(a) (by adding proportional amounts of materials in Example 6) are transferred to a jacketed mix tank. The solution is mixed at low speed for 4 hours (at ambient pressure) to deaerate, while heating the tank to maintain a solution temperature of about 45° C. 96 kg of red pea starch-based dipping solution prepared in accordance with Example 6(b) (by adding proportional amounts materials from Example 6) are transferred to a first feed tank. Red gel-dipping solution is then transferred to a second feed tank. Material from each feed tank is allowed to flow into a separate dip pan.

Part (2):
Subcoated cores prepared according to Example 5 (2.7% subcoating level), are transferred to the hopper of the gel-dipping apparatus described in U.S. Pat. No. 5,234,099.

Part (3):
A first end of each subcoated core is dipped into yellow gel-dipping solution, and a second end of each subcoated core is dipped into the second red gel-dipping solution, according to the method and using the apparatus described in U.S. Pat. No. 5,234,099. The dipping operation is carried out using the following operating limits:

Supply air temperature: 25-32° C.
Supply air dew point: 9-11° C.
Supply air volume: 9500-10500 CFM
Dip area temperature 19-22° C.
Dip area air volume 250-350 CFM
Dip pan Temperatures ($1^{st}$ and 2nd): 42.0-45.0° C.
Yellow (1) gel-dipping solution viscosity: 1280 cps
Red (2) gel-dipping solution viscosity: 1280 cps
Depth of dip to cutline (first blue end): 0.320"-0.333"
Depth of dip to cutline (second blue end): 0.320"-0.335"
Moisture content (% loss on drying at 150° C.) of finished gelcaps: 2.0%
Gel-dipped coating level (% by weight of subcoated cores): 4%

Part (4):
The dipped caplets containing an overlapping seam are then transferred to a hopper.

Part (5):
A second portion of caplets is coated with an exposed portion of the subcoat, also known as "short-dipped" gelcaps. The "short-dipped" gelcaps are then transferred to the hopper of a Hartnett Delta Printer equipped with a Transverse-Excited Atmospheric (TEA) CO2 laser (RW Hartnett Company, Philadelphia, Pa.). The wavelength that used is approximately 10.6 nanometers, and the pulse duration is approximately 10 microseconds. Any shape hole can be produced by means of placing a mask in the path of the laser beam. For the sake of ease of calculations, a simple circle is used to create a hole in the subcoated portion only. The diameter size of the hole on the tablet can be varied from 1.5 mm to 2.0 mm. The larger the area ablated by the laser, the more energy required.

Part (6):
A portion of the dipped caplets containing an overlapping seam from Example 7(c)(Part 4) is also transferred to a hopper of a Hartnett Delta Printer equipped with a Transverse-Excited Atmospheric (TEA) CO2 laser. The wavelength that used is approximately 10.6 nanometers, and the pulse duration is approximately 10 microseconds. A simple circle is then created which extends through the top dipped coating to the core.

Example 8

Surface Gloss Measurement of Coated Tablets

Coated and uncoated tablets described below were tested for surface gloss using an instrument available from TriCor Systems Inc. (Elgin, Ill.) under the tradename, "Tri-Cor Model 805A/806H Surface Analysis System" generally in accordance with the procedure described in "TriCor Systems WGLOSS 3.4 Model 805A/806H Surface Analysis System Reference Manual" (1996), which is incorporated by reference herein, except as modified below.

The instrument utilized a CCD camera detector, employed a flat diffuse light source, compared tablet samples to a reference standard, and determined average gloss values at a sixty (60) degree incident angle. During operation, the instrument generated a gray-scale image, wherein the occurrence of brighter pixels indicated the presence of more gloss at that given location. The instrument also incorporated software that utilized a grouping method to quantify gloss, i.e., pixels with similar brightness were grouped together for averaging purposes.

The "percent full scale" or "percent ideal" setting (also referred to as the "percent sample group" setting), was specified by the user to designate the portion of the brightest pixels above the threshold that will be considered as one group and averaged within that group. "Threshold", as used herein, is defined as the maximum gloss value that will not be included in the average gloss value calculation. Thus, the background, or the non-glossy areas of a sample were excluded from the average gloss value calculations. The method disclosed in K. Fegley and C. Vesey, "The Effect of Tablet Shape on the Perception of High Gloss Film Coating Systems", Colorcon (West Point, Pa. USA) (2002) and incorporated by reference herein, was used in order to minimize the effects resulting from different tablet shapes, and thus report a metric that was comparable across the industry. (Selected the 50% sample group setting as the setting which best-approximated analogous data from tablet surface roughness measurements.).

After initially calibrating the instrument using a calibration reference plate (190-228; 294 degree standard; no mask, rotation 0, depth 0), a standard surface gloss measurement was then created using gel-coated caplets available from McNeil-PPC, Inc. under the tradename, "Extra Strength Tylenol Gelcaps." The average gloss value for a sample of 112 of such gel-coated caplets was then determined, while employing the 25 mm full view mask (190-280), and configuring the instrument to the following settings:

Rotation: 0
Depth: 0.25 inches
Gloss Threshold: 95
% Full Scale: 50%
Index of Refraction: 1.57

The average surface gloss value for the reference standard was determined to be 269, using the 50% ideal (50% full scale) setting. Commercially available gel coated tablets were tested in accordance with the above procedure. The results are summarized in table below.

TABLE 2

Gloss values of Caplets

| Sample | Coating Method - Type | Samples tested | Average Gloss Value |
|---|---|---|---|
| Tylenol ES RRG[2] | Dipped - Gelatin | 5 | 316 |
| Tylenol Sinus RRG[3] | Dipped - Gelatin | 5 | 323 |
| Subcoated Core[1] | Sprayed Film - HPMC Based | 5 | 167 |
| Example 7A | Dipped - Red/Blue Pea Starch Based | 5 | 325 |
| Example 7B | Dipped - Red/Yellow Pea Starch Based | 5 | 321 |

[2]Tylenol ES RRG Commercially available Tylenol Extra Strength Rapid Release Gels
[3]Tylenol Sinus RRG Commercially available Tylenol Sinus Rapid Release Gels
[1]Subcoated Core prepared in accordance with Example 5
HPMC Hypromellose Example 9

Dissolution Analysis of Gelcaps Coated with Pea Starch Based Dip-Coating

All dissolutions for acetaminophen are analyzed using the following dissolution parameters: USP Type II apparatus (paddles, 50 RPM) in pH 5.8 Phosphate Buffer at 37° C. Sample aliquots of approximately 10 mL are analyzed at 15 and 30 minutes using a UV spectrophotometer set at a wavelength of 243 nm using a 0.02 cm flow-cell. The test result is shown in the Figure below.

Example 10

Preparation of Red Corn-Starch Based Dipping Solution 829.26 kg of sterile water for irrigation are added to a 50-gallon stainless steel vessel. With agitation at 80 RPM, 0.576 kg of locust bean gum and 0.806 kg of xanthan gum are added orderly. Then, the mixture is heated to 85° C. At 85° C., 248.417 kg of corn starch are added and mixed for 1 hour. After that, 24.971 kg of glycerin, 1.658 kg of sodium lauryl sulfate, and 13.82 kg of red colorant are added. The solution is mixed at low speed for 4 hours (at ambient pressure) to deaerate while the tank is maintained at a solution temperature of about 45° C.

Example 11

Preparation of Blue Corn-Starch Based Dipping Solution 829.26 kg of sterile water for irrigation are added to a 50-gallon stainless steel vessel. With agitation at 80 RPM, 0.576 kg of locust bean gum and 0.806 kg of xanthan gum are added orderly. Then, the mixture is heated to 85° C. At 85° C., 248.417 kg of corn starch are added and mixed for 1 hour. After that, 24.971 kg of glycerin, 1.658 kg of sodium lauryl sulfate and 13.82 kg of blue colorant are added. The solution is mixed at low speed for 4 hours (at ambient pressure) to deaerate while the tank is maintained at a solution temperature of about 45° C. These coated forms are tested using the Gloss analysis described in Example 8.

TABLE 3

Comparison of Two Starch Based Dip Coated Formulations

| Coating Type | % Solids | Viscosity @ 45° C. (cps) | Gloss Value | Observation |
|---|---|---|---|---|
| Corn Starch | 25* | 2950* | 289 | Dried Film Cracked |
| Pea Starch | 30 | 1327 | 310 | Dried Film Intact |

*Due to viscosity limitations a lower % solids must be utilized to perform a coating comparison.

Thus, the high amylose, pea starch containing coating had a higher gloss value and did not crack as compared to the corn starch containing coating. Cereal starches, such as corn starch, contain approximately 25 to 29 percent amylose. See Hilbert et al., J. Biol Chem 162(2):229 (1946).

What is claimed is:

1. A method of making a coated tablet, said method comprising dipping a core comprising an active agent into a coating liquid and drying said dipped core to form an outer-coating on said core, wherein said coating liquid comprises at least one starch having an amylose content of at least about 50 percent by weight of said starch, wherein said at least one starch is a pea starch, wherein said coating liquid additionally comprises at least one gum, wherein the weight ratio of said at least one starch to said at least one gum is from about 250:1 to about 100:1, and wherein said coating liquid comprises, based upon the total weight of the coating liquid, from about 10 percent to about 40 percent of said at least one starch.

2. A method of claim 1, wherein said at least one gum is selected from the group consisting of xanthan gum, locust bean gum, tara gum, and mixtures thereof.

3. A method of claim 1, wherein said coating liquid comprises both xanthan gum and locust bean gum.

4. A method of claim 1, wherein said coating liquid additionally comprises at least one plasticizer.

5. A method of claim 4, wherein said plasticizer is selected from the group consisting of glycerin, propylene glycol, polyethylene glycol, triethyl citrate and tributyl citrate.

6. A method of claim 1, wherein said coating liquid comprises, based upon the total weight of the coating liquid,
   a) from about 0.01 percent to about 0.5 percent of locust bean gum;
   b) from about 0.01 percent to about 0.5 percent of xanthan gum; and
   c) from about 1 percent to about 10 percent of glycerin.

7. A method of claim 1, wherein said core has a first end and a second end, and said method comprising dipping said first end of the core into said coating liquid and drying said dipped first end to form a outer-coating on said first end and said method further comprises dipping said second end in a second coating liquid and drying said dipped second end to form a second outer-coating on said second end, wherein said second coating liquid also comprises at least one said starch and wherein said second coating liquid is a different color from said first coating liquid.

8. A method of claim 1, wherein said method further comprises creating one or more openings in said coating to expose said core on the surface of said coated tablet.

9. A method of claim 1, wherein the viscosity of the coating liquid is from about 400 to about 3000 cps.

10. A method of claim 1, wherein said liquid medium comprises water.

11. A method of claim 1, wherein the percent solids of the coating liquid is from about 20 percent to about 45 percent.

12. A coated tablet manufactured by the method of claim 1.

13. A coated tablet of claim 12, wherein the resulting outer-coating comprises, based upon the total dried weight of the outer-coating, from about 75 percent to about 99 percent of said at least one starch.

14. A coated tablet of claim 12, wherein said coating comprises, based upon the total dried weight of the coating,
   a) from about 70 percent to about 99 percent of pea starch having an amylose content of at least about 50 percent by weight of said starch;
   b) from about 0.05 percent to about 1 percent of locust bean gum;
   b) from about 0.05 percent to about 1 percent of xanthan gum; and
   c) from about 0.5 percent to about 15 percent of glycerin.

15. A method of claim 1, wherein said core comprises a subcoating.

16. A method of claim 3, wherein said core comprises a subcoating.

17. A method of claim 6, wherein said core comprises a subcoating.

* * * * *